(12) United States Patent
Kwok et al.

(10) Patent No.: US 7,363,074 B1
(45) Date of Patent: Apr. 22, 2008

(54) COATINGS COMPRISING SELF-ASSEMBLED MOLECULAR STRUCTURES AND A METHOD OF DELIVERING A DRUG USING THE SAME

(75) Inventors: Connie S. Kwok, Sunnyvale, CA (US); Charles D. Claude, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 953 days.

(21) Appl. No.: 10/225,025

(22) Filed: Aug. 20, 2002

(51) Int. Cl.
*A61N 1/30* (2006.01)

(52) U.S. Cl. .................. 604/20; 524/70; 604/501

(58) Field of Classification Search ............. 424/422; 604/20, 501
See application file for complete search history.

(56) References Cited

U.S. PATENT DOCUMENTS

| | | | | |
|---|---|---|---|---|
| 4,096,238 A * | 6/1978 | Zaffaroni et al. | ............ | 424/467 |
| 4,327,008 A * | 4/1982 | Schimmel et al. | ........... | 524/104 |
| 4,513,034 A * | 4/1985 | Sparer et al. | ................. | 428/1.6 |
| 4,968,539 A * | 11/1990 | Aoyagi et al. | ............... | 428/1.5 |
| 4,977,901 A | 12/1990 | Ofstead | ....................... | 128/772 |
| 5,112,457 A | 5/1992 | Marchant | ..................... | 204/165 |
| 5,328,471 A | 7/1994 | Slepian | ........................ | 604/101 |
| 5,455,040 A | 10/1995 | Marchant | ..................... | 424/426 |
| 5,464,650 A | 11/1995 | Berg et al. | .................... | 427/2.3 |
| 5,578,073 A | 11/1996 | Haimovich et al. | ............ | 623/1 |
| 5,605,696 A | 2/1997 | Eury et al. | .................... | 424/423 |
| 5,667,767 A | 9/1997 | Greff et al. | ............... | 424/9.411 |
| 5,670,558 A | 9/1997 | Onishi et al. | ................. | 523/112 |
| 5,700,286 A | 12/1997 | Tartaglia et al. | ............... | 623/1 |
| 5,716,981 A | 2/1998 | Hunter et al. | ................ | 514/449 |
| 5,824,049 A | 10/1998 | Ragheb et al. | .................. | 623/1 |
| 5,830,178 A | 11/1998 | Jones et al. | .................... | 604/49 |
| 5,837,313 A | 11/1998 | Ding et al. | ..................... | 427/2.21 |
| 5,851,508 A | 12/1998 | Greff et al. | ............... | 424/9.411 |
| 5,858,746 A | 1/1999 | Hubbell et al. | ............ | 435/177 |
| 5,865,814 A | 2/1999 | Tuch | ........................ | 604/265 |
| 5,869,078 A * | 2/1999 | Baudino | .................... | 424/423 |
| 5,873,904 A | 2/1999 | Ragheb et al. | .................. | 623/1 |
| 5,971,954 A | 10/1999 | Conway et al. | ............... | 604/96 |
| 5,980,928 A | 11/1999 | Terry | ......................... | 424/427 |
| 5,980,972 A | 11/1999 | Ding | .......................... | 427/2.24 |
| 6,015,541 A | 1/2000 | Greff et al. | ................. | 424/1.25 |
| 6,042,875 A | 3/2000 | Ding et al. | .................. | 427/2.24 |
| 6,051,648 A | 4/2000 | Rhee et al. | ................. | 525/54.1 |
| 6,056,993 A | 5/2000 | Leidner et al. | ............. | 427/2.25 |
| 6,060,451 A | 5/2000 | DiMaio et al. | ................ | 514/13 |
| 6,080,488 A | 6/2000 | Hostettler et al. | ........ | 428/423.3 |
| 6,096,070 A | 8/2000 | Ragheb et al. | .................. | 623/1 |
| 6,099,562 A | 8/2000 | Ding et al. | ................. | 623/1.46 |
| 6,110,188 A | 8/2000 | Narciso, Jr. | ................. | 606/153 |
| 6,113,629 A | 9/2000 | Ken | ............................. | 623/1.1 |
| 6,120,536 A | 9/2000 | Ding et al. | ................. | 623/1.43 |
| 6,120,904 A | 9/2000 | Hostettler et al. | ........ | 428/423.3 |
| 6,121,027 A | 9/2000 | Clapper et al. | ............. | 435/180 |
| 6,129,761 A | 10/2000 | Hubbell | ....................... | 623/11 |
| 6,153,252 A | 11/2000 | Hossainy et al. | ............ | 427/2.3 |
| 6,165,212 A | 12/2000 | Dereume et al. | .......... | 623/1.13 |
| 6,444,217 B1 | 9/2002 | Kwok et al. | ................. | 424/423 |
| 6,468,657 B1 * | 10/2002 | Hou et al. | ................... | 428/403 |
| 6,490,483 B2 * | 12/2002 | Willis | .......................... | 604/20 |
| 6,730,016 B1 * | 5/2004 | Cox et al. | ..................... | 600/37 |
| 7,114,312 B2 * | 10/2006 | Coppeta et al. | ............... | 53/471 |
| 2002/0138123 A1 * | 9/2002 | Casas-Bejar et al. | ....... | 607/120 |

FOREIGN PATENT DOCUMENTS

| | | |
|---|---|---|
| EP | 0 665 023 | 8/1995 |
| EP | 0 970 711 | 1/2000 |
| WO | WO 00/12147 | 3/2000 |
| WO | WO 00/64506 | 11/2000 |
| WO | WO 01/01890 | 1/2001 |

OTHER PUBLICATIONS

Kwon et al., "Electrically erodible polymer gel for controled release of drugs," 2001, Nature, vol. 354, 291-293.*
Bae et al., "Pulsatile Drug Release by electric Current," 1994, ACS Symposium Series, vol. 545, pp. 98-110.*
Kwok et al., "Surface Modification of Polymers with self-Assembled Molecular Structures: Multitechnique Surface Characterization," 2000, Biomacromolecules, vol. 1, pp. 139-148.*
Labhasetwar et al., "Iontophoresis for modulation of cardiac drug delivery in dogs," 1995, PNAS, vol. 92, pp. 2612-2616.*
Kwok et al., "Self-Assembled molecular structures as ultrasonically-responsive barrier membranes for pulsatile drug delivery," 2001, 27th Annual Meeting of the Society for Biomaterials, pp. 151-163.*

(Continued)

*Primary Examiner*—Michael Woodward
*Assistant Examiner*—Bethany Barham
(74) *Attorney, Agent, or Firm*—Squire Sanders & Dempsey, LLP

(57) ABSTRACT

A coating for an implantable medical device is disclosed, the coating including a self-assembled molecular structure. The coating can be used for altering the release rate of a therapeutic substance from the implantable device.

13 Claims, No Drawings

OTHER PUBLICATIONS

"Clinical Cardiac Pacing" editors: Ellenbogan, KA; Kay, GN; and Wilkoff, BL (2000) p. 132-137, 562-563, 966-969.*

Takashi Kato "Self-Assembly of Phase-Segregated Liquid Crystal Structures", Science, Mar. 29, 2002, vol. 295, No. 5564, p. 2414-2418.*

Mirfakhrai et al; "Polymer artificial muscles", Materials Today (Apr. 2007), vol. 10, No. 4, p. 30-38.*

Kwok et al., *Self-Assembled Molecular Structures As Ultrasonically-Responsive Barrier Membranes For Pulsatile Drug Delivery*, J. Biomed. Mater. Res. 57:151-164 (2001).

Kwok et al., *Surface Modification Of Polymers With Self-Assembled Molecular Structures: Multitechnique Surface Characterization*, Biomacromolecules 1:139-148 (2000).

* cited by examiner

COATINGS COMPRISING SELF-ASSEMBLED MOLECULAR STRUCTURES AND A METHOD OF DELIVERING A DRUG USING THE SAME

BACKGROUND

1. Field of the Invention

This invention is directed to coatings for implantable medical devices, such as pacing leads.

2. Description of the State of the Related Art

Pacing leads are widely used for treatment of a variety of heart ailments, for example, irregularity of the heart beat. It is desirable to be able to use the pacing lead not only for defibrillation, but also as a vehicle for providing biological therapy.

Biological therapy can be achieved by medicating pacing leads. One method for medicating pacing leads involves the use of a polymeric carrier coated onto the surface of a pacing lead. A solution which includes a solvent, a polymer dissolved in the solvent, and a therapeutic substance dispersed in the blend is applied to the pacing lead. The solvent is allowed to evaporate, leaving on the pacing lead surface a coating of the polymer and the therapeutic substance impregnated in the polymer.

For the purposes of pharmacological therapy, it is important to maintain the concentration of the drug at a therapeutically effective level for an acceptable period of time. Hence, controlling a rate of release of the drug from the pacing lead is important, especially in such a way so as to decrease the release rate of the drug from the underlying matrix. It is also desirable to be able to rapidly increase the rate of release of the drug during the process of defibrillation, and then to return quickly to slow delivery of the drug.

In view of the foregoing, coatings capable of pulsatile drug delivery from pacing leads, are desired. Embodiments of the present invention disclose such coatings and methods for fabricating thereof.

SUMMARY

According to one embodiment of the present invention, a coating for an implantable medical device is provided, the coating comprises a polymer layer having a crystalline structure, wherein the structure of the polymer becomes less crystalline when the polymer is exposed to a stimulus, and wherein, when the stimulus is terminated, the structure of the polymer returns back to essentially the same degree of crystallinity or a more crystalline structure than that of when the polymer was exposed to the stimulus. The polymer layer can be prepared from a compound which includes a methylene-based chain or a silicone-based chain and at least one reactive functional group, for example, octadecyl isocyanate or 1-octadecanol.

According to another embodiment of the present invention, a method for local delivery of a drug is provided, the method comprises implanting a medical device carrying a drug-containing coating in a patient for the sustained local delivery of the drug and applying an electric current for an interval of time to the device for increasing a rate of delivery of the drug. The coating comprises a polymeric reservoir layer disposed on at least a portion of the device, and a layer of a self-assembled structure of molecules of an organic or elemento-organic substance bonded to the reservoir layer. The reservoir layer is made from a polymer which includes at least one reactive functional group, for example, from poly(ethylene-co-vinyl alcohol), poly(methyl methacrylate-co-2-hydroxyethyl methacrylate), poly(2-hydroxyethyl methacrylate), or poly(amino acid).

DETAILED DESCRIPTION

A coating for an implantable medical device, such as a pacing lead, can be applied onto the device using conventional coating techniques, for example, spraying or dipping. According to one embodiment of the present invention, the coating can include a drug-polymer layer (also referred to as "a reservoir layer"), a topcoat layer, and an optional primer layer. The drug-polymer layer can be applied directly onto the surface of the pacing lead to serve as a reservoir for an active agent (or a drug) which is incorporated into the reservoir layer. The optional primer layer can be applied between the device and the reservoir layer to improve the adhesion of the reservoir layer to the device. The topcoat membrane layer can be applied over the reservoir layer. The topcoat layer, which can be essentially free from any therapeutic substances or drugs, serves as a rate limiting membrane which further controls the rate of release of the drug. By forcing the agent to diffuse through an additional coating layer, the release of the active agent may be slowed.

The topcoat layer is made of a self-assembled molecular structure (SAMS). For the purposes of this invention, SAMS is defined as a thin crystalline film of an ordered structure of molecules of an organic or elemento-organic substance. The thin film forms on a surface of a substrate when the surface is exposed to the molecules of the substance at suitable reaction conditions. One of the conditions can be addition of catalysts. "Ordered structure" is defined as a closely packed structure, being for example about 4 Å apart, and can display a tilt angle of between about 30° and 35° from the normal of the substrate. "Thin" is defined as a layer having a thickness on a micron scale, from about 0.1 to about 5 µm.

At ambient temperature, SAMS serves as a barrier effectively preventing the drug from significantly diffusing out of the coating prior to deployment of the coated pacing lead (e.g., during storage and transportation of the coated pacing lead). After the pacing lead has been placed into a human body, the pacing lead coated with the coating which includes a SAMS can be operated as a drug delivery vehicle capable of a dual mode pulsatile delivery.

In the first mode of delivery, the release regime can be either zero release or steady background release, depending on the chemical components forming the SAMS. In this mode, after the coated pacing lead has been placed into the patient's body, the pacing lead becomes exposed to the body temperature (approximately 37° C.). At such temperature, the SAMS undergoes at least a partial transformation. The transformation leads to creating a molecular structure which is still predominantly crystalline but includes some amorphous portions, allowing the drug to start steadily eluting at a slow and substantially constant rate from the pacing lead.

In the second mode of delivery, the drug is delivered in a "burst" regime. The burst mode can be used when it is desirable to provide for a short period of a more substantial rate of release. For the purposes of the present invention the term "burst" mode of delivery is defined as a regime where a release rate is at least twice as high as the background release rate.

The pacing lead can be used for treatments of arrhythmia. When the heart rhythm of a patient becomes irregular and has to be corrected, an electric signal is generated at an electrode of the pacing lead to correct the rhythm. This treatment technique is known to those having ordinary skill in the art. It can be beneficial for the patient to receive an increased dose of medication while the heart rhythm is being corrected. The burst delivery mode allows for delivery of such increased dose for a short period of time.

During the process of correction of the heart rhythm, the electric signal can also lead to inducing further crystalline/amorphous transition of the SAMS. As a result, the barrier properties of the topcoat layer made of a SAMS can be significantly reduced allowing the rapid release of the drug. When the electric signal is terminated, the SAMS self-heals quickly, restoring the initial predominantly crystalline structure. Therefore, after the electric signal is terminated, the barrier properties of the SAMS-based topcoat membrane are essentially restored, returning the device to the first mode of delivery.

The electric signal, that is sent to the electrode of the pacing lead, typically has parameters used in defibrillating devices, for example, a current of about 15 Amperes, voltage of about 700 Volts, and a pulse duration of about 10 milliseconds. The cyclic process of applying the electric current can be repeated as often as necessary.

Examples of suitable substance that can be used to prepare SAMS include substances having a general formula (I)

$$R\text{-}A\text{-}R' \qquad (I),$$

where A represents a methylene chain or a silicone chain, and R and R' are functional groups, at least one of which is a reactive functional group.

SAMS can be prepared by applying substance (I) on a device having reservoir layer deposited over at least a portion of the device. For the purposes of the present invention, substance (I) is referred to as a "SAMS-forming substance." Any suitable SAMS-fabrication technique known to those having ordinary skill in the art can be used. For example, a SAMS-forming substance can be applied from a solution. Typically, a SAMS-forming substance can be dissolved in an appropriate solvent, such as tetrahydrofuran (THF) or hexanes. The concentration of the SAMS-forming substance in the solution can be typically between 1 and 10% by volume. The device can then be immersed into the solution, usually for a short period of time which can be between about 30 minutes and a few hours, followed by rinsing with a solvent, e.g. THF, to remove the unreacted residues, and vacuum drying.

According to one embodiment of the present invention, methylene chain-based SAMS can be used to form the topcoat layer. For the methylene chain-based SAMS, "A" in formula (I) is the methylene group —$CH_2$—. Thus, the methylene chain-based SAMS comprises a methylene chain having functional groups on both ends of the chain. The structure of a substance forming a SAMS can be represented by a general formula (II)

$$R\text{—}(CH_2)_n\text{—}R', \qquad (II)$$

where the substitutents are the same (R=R') or different (R≠R'). Methylene chains can typically include between 10 and 25 carbon atoms (n=10–25). R and/or R' can usually include hydrogen, methyl, hydroxyl, carboxyl, sulfonyl, acetate, trifluoro acetate, benzoate, isocyanate, epoxy, amino, thiol, or acrylic groups. At least one of R and R' is a reactive group. For example, if R is methyl (a non-reactive group), R' will be a reactive group, e.g., hydroxyl, isocyanate or epoxy group.

SAMS can be chemically bonded to the reservoir layer. To bond the SAMS, covalent bonds are formed between the SAMS and the reservoir layer using the functionalities present in the SAMS-forming substance and in the polymer forming the reservoir layer.

One example of a polymer having functional groups that can be used for bonding SAMS is poly(ethylene-co-vinyl alcohol) having a general formula —$[CH_2\text{—}CH_2]_p$—$[CH_2\text{—}CH(OH)]_q$—, where "p" and "q" are integers. Poly(ethylene-co-vinyl alcohol) is known under the trade name EVAL and is manufactured by EVAL Company of America of Lisle, Ill. EVAL is also distributed commercially by Aldrich Chemical Company of Milwaukee, Wis.

EVAL is a product of hydrolysis of ethylene-vinyl acetate copolymers. Those having ordinary skill in the art of polymer chemistry will understand that EVAL may also be a terpolymer and may include up to 5% (molar) of units derived from styrene, propylene and other suitable unsaturated monomers.

The hydroxyl functionality of EVAL can be used for chemical bonding SAMS. Instead of EVAL, other polymers having hydroxyl groups can be utilized for preparing the reservoir layer and for bonding SAMS. Other examples of such polymers include poly(butyl methacrylate-co-2-hydroxyethyl methacrylate) [P(BMA-HEMA)] having the formula $$-[CH_2-\underset{\underset{OC_4H_9}{\overset{\overset{CH_3}{|}}{C}}}{\overset{|}{C}}]_x-[CH_2-\underset{\underset{OCH_2-CH_2-OH}{\overset{\overset{CH_3}{|}}{C}}}{\overset{|}{C}}]_y-$$

and poly(2-hydroxyethyl methacrylate) (PHEMA) having the formula $$-[CH_2-\underset{\underset{OCH_2-CH_2-OH}{\overset{\overset{CH_3}{|}}{C}}}{\overset{|}{C}}]_z-$$

where "x," "y," and "z" are integers.

According to one embodiment, an isocyanate-terminated SAMS-forming substance can be bonded to a reservoir polymer containing hydroxyl groups. In the isocyanate-terminated SAMS-forming substance, at least one of R and R' in formula (I) is the isocyanate group —N=C=O. Examples of suitable isocyanate-terminated SAMS-forming substances that can be bonded to the polymer of the reservoir layer include octadecyl isocyanate and dodecyl isocyanate.

Due to the presence of the isocyanate groups, the isocyanate-terminated SAMS-forming substance is chemically very active and readily reacts with EVAL. The isocyanate group, having strong electron accepting properties, reacts with nucleophilic hydroxyl group of EVAL, as illustrated in case of octadecyl isocyanate by reaction scheme (III):

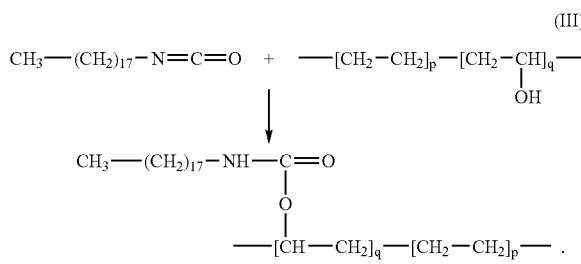

(III)

The conditions under which reaction (III) is conducted can be determined by those having ordinary skill in the art. For example, the reaction can be carried by preparing a solution of octadecyl isocyanate and adding the solution to EVAL. The temperature can be maintained at between about 40° C. and about 60° C., and the reaction can be conducted for not more than about 1 hour.

Since the isocyanate group easily becomes inactive as a result of hydrolysis, reaction (III) is conducted in an inert water- and moisture-free environment, for example, under dry nitrogen or argon atmosphere using anhydrous hexane or tetrahydrofuran as the solvent for octadecyl isocyanate. The reaction can be catalyzed by adding to the solution of octadecyl isocyanate between about 0.1 mass % and about 0.5 mass %, for example, about 0.3 mass % of the catalyst dibutyltin dilaurate having the formula $[CH_3—(CH_2)_{10}—C(O)O]_2Sn[(CH_2)_3—CH_3]_2$ or by adding another suitable catalyst.

If desired, EVAL can be replaced with another acceptable polymer containing hydroxyl groups. For example, isocyanate-terminated SAMS-forming substance can be bonded to PHEMA utilizing hydroxyl groups of the PHEMA. As a result, the SAMS is firmly bonded to EVAL or another acceptable hydroxyl-containing polymer to form the urethane product of reaction (III).

According to another embodiment of the present invention, instead of a polymer containing hydroxyl groups, a polymer containing alternative functional groups can be used for making the reservoir layer. The alternative functional groups can be used to bond a SAMS-forming substance to the reservoir layer. Examples of suitable alternative groups include amino groups, carboxyl groups and thiol groups.

One example of a polymer containing amino groups that can be used for making the reservoir layer is poly(amino acid). To bond a SAMS-forming substance to this reservoir layer, the alkylation of amines technique can be used. In this case, the SAMS-forming substance provides the hydroxyl functionality and the reservoir polymer provides the amino functionality. The SAMS-forming substance can be a hydroxyl-terminated compound, such as a long-chained aliphatic alcohol or diol which can be represented as formula (II), where either R or R', or both, is a hydroxyl group. Examples of such compounds include 1-octadecanol (also known as stearyl alcohol), and dodecanol.

To bond 1-octadecanol to the aminated reservoir, as a first step 1-octadecanol can be preliminarily derivatized by tosylation (treatment with tosyl chloride), or alternatively by tresylation (by reacting with tresyl chloride). Tosyl chloride (TsCl) is a sulfonyl derivative of toluene, p-toluenesulfonyl chloride, having the formula $CH_3—C_6H_4—SO_2Cl$. Tresyl chloride or 2,2,2-trifluoroethanesulphonyl chloride (TrCl) is an aliphatic derivative of sulfonic acid having the formula $CF_3—CH_2—SO_2Cl$. The conditions under which the tosylation or tresylation is carried are known to those having ordinary skill in the art.

As a result of tosylation, tosyl group is attached to 1-octadecanol via hydroxy group to yield the toluenesulfoester as illustrated by reaction (IV):

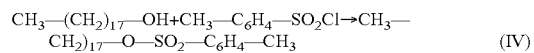

(IV)

Alternatively, if tresylation is used to derivatrize 1-octadecanol, the process can be illustrated as shown by reaction (V) and as a result the tresyl group is attached to 1-octadecanol via hydroxyl group:

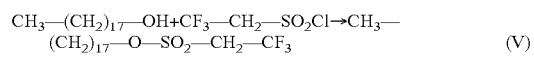

(V)

As a second step of conjugating, the aminated polymer of the reservoir is reacted with the derivatized 1-octadecanol. Since toluenesulfonic acid is known to be a very strong acid, its anion, $CH_3—C_6H_4—SO_3—$, is an excellent leaving group in the nucleophilic substitution alkylation reaction of a primary amine. Accordingly, the tosylated 1-octadecanol (the product of reaction (IV) obtained as described above), readily reacts with the aminated polymer of the reservoir as schematically shown by the alkylation reaction (VI):

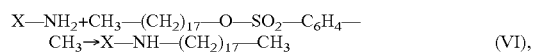

(VI), where X symbolizes the backbone of the polymer forming the reservoir.

The conditions under which reaction (VI) is conducted can be determined by those having ordinary skill in the art. The reaction of tresylated 1-octadecanol and the aminated polymer forming the reservoir layer is similar to reaction (VI). As a result, 1-octadecanol is bonded to the polymer of the reservoir layer to form the secondary amine product of reaction (VI).

Instead of the hydroxyl-terminated SAMS-forming substance, a carboxyl-terminated SAMS-forming substance can be used, for example a carbonic acid. In such a case, the carboxyl-terminated SAMS-forming substance can be conjugated to the amino group-containing polymer of the reservoir layer to form an amide, under conditions that can be determined by those having ordinary skill in the art.

The polymer of the reservoir layer can be any polymer otherwise suitable for making coatings for implantable medical devices such as pacing leads. The above-described embodiments discuss reservoir layers made of polymers that include a reactive group, such as hydroxyl, amino, or acrylate group. However, the polymers not having reactive groups can be also used to make the reservoir layer. Polymers without reactive groups can be pre-treated to generate the reactive groups so as to enable the bonding of the SAMS-forming substance to the polymer of the reservoir layer.

For example, hydroxyl groups can be generated on the surface of a reservoir layer not originally containing hydroxyl groups by partially oxidizing the polymer forming the reservoir layer. The partial oxidation can be accomplished using low energy surface treatments known to those having ordinary skill in the art. Examples of such treatments include oxidative gas plasma treatment, corona discharge and electron beam treatment, oxidative gas treatments using, for example, ozone or a mixture of fluorine and oxygen, and chemical etching treatments using, for example, nitric acid or chromic acid.

In another embodiment, amino groups can be generated on the surface of a reservoir layer not originally containing amino groups. For example, the surface of the reservoir polymer can be treated by oxygen plasma to generate aldehyde or ketone groups, followed by reaction with hydroxylamine $NH_2$—OH and reduction yielding amino groups on the surface of the reservoir polymer. Alternatively, the surface of the reservoir polymer can be treated with ammonium and hydrogen gas plasma to generate amino groups.

In addition to EVAL, PHEMA, P (BMA-HEMA), and poly(amino acid) discussed above, representative examples of polymers that can be used to fabricate the reservoir layer include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D, L-lactic acid), poly(glycolic acid-co-trimethylene carbonate), polyphosphoester, polyphosphoester urethane, cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes (such as CORETHANE available from Pfizer Corp. of New York or ELASTEON available from AorTech Biomaterials Co. of Chatswood, Australia), silicones, polyesters, polyolefins, polyisobutylene and ethylene-alphaolefin copolymers, acrylic polymers and copolymers (such as poly(butyl methacrylate), poly(ethyl methacrylate) or poly(hydroxyethyl methacrylate)), vinyl halide polymers and copolymers (such as polyvinyl chloride), polyvinyl ethers other than polyacetals, polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. If the selected polymer does not have reactive groups, it can be treated as discussed above to introduce the desired reactive groups.

The drug-containing reservoir layer can be formed on the pacing lead in any suitable manner. For example, a coating composition including a solvent, a polymer, and the drug can be applied to the pacing lead by immersing the pacing lead in the coating composition or by spraying the coating composition onto the pacing lead. Following evaporation of the solvent, a reservoir layer of the polymer and the drug incorporated in the polymer is formed on the pacing lead.

Alternatively, a polymeric reservoir layer, free from drugs, can be formed on the pacing lead by any suitable method. The drug can then be introduced into the reservoir layer by, for example, placing the coated pacing lead into a reaction flask containing the drug, allowing the agent to diffuse across the concentration gradient into the reservoir layer, and drying the pacing lead to form an drug-containing reservoir layer on the pacing lead.

The drug that can be used in the pacing lead coating can include anti-inflammatory corticoids, for example, dexamethasone acetate or dexamethasone sodium phosphate. Although the present invention has been described with reference to a pacing lead, SAMS can also be used in conjunction with other implantable devices such as stents.

EXAMPLES

Some embodiments of the present invention are further illustrated by the following example.

Example 1

A composition can be prepared by mixing the following components:
(a) about 2.0 mass % of EVAL;
(b) about 0.7 mass % of dexamethasone acetate; and
(c) the balance, DMAC solvent.

The composition can be applied onto the surface of a pacing lead, for example, FLEXEXTEND available from Guidant Corp., by spraying and dried to form a drug-polymer (reservoir) layer. A spray coater can be used, having a 0.014 inch fan nozzle maintained at about 60° C. with a feed pressure of about 0.2 atm (about 3 psi) and an atomization pressure of about 1.35 atm (about 20 psi). An total of about 500 μg of the wet coating can be applied. The drug-polymer layer can be baked at about 50° C. for about two hours.

The pacing lead coated with the drug-polymer layer as described above, can be placed in a round bottom flask. About 1 ml of a SAMS-forming material, for example, octadecyl isocyanate, and about 20 ml of a poor-swelling anhydrous solvent, such as THF, can be added to the flask. The contents of the flask are kept in an inert atmosphere, for example, nitrogen or argon atmosphere.

The solution contained in the flask is heated, for example, to about 60° C., and a catalyst, for example dibutyltin dilaurate can be added to the solution. The amount of catalyst can be about 0.3 mass % of the weight of octadecyl isocyanate. The reaction can be maintained for about 30 minutes at about 60° C. to yield a SAMS formed on the pacing lead, followed by rinsing with fresh THF and vacuum drying.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for local delivery of a drug, comprising acts of: (a) implanting a medical device carrying a drug-containing coating in a patient for the sustained local delivery of the drug, wherein the coating comprises a polymeric reservoir layer disposed on at least a portion of the device, and a layer of a self-assembled structure of molecules of an organic or elemento-organic substance bonded to the reservoir layer; and (b) applying an electric current for an interval of time to the device to cause the self-assembled structure of molecules to transform from a crystalline structure to an amorphous structure so as to increase for increasing the rate of release of the drug, wherein after the electric current is terminated, the crystallinity of the self-assembled structure of molecules returns back to essentially the same degree of crystallinity or a more crystalline structure than that of when the self-assembled structure of molecules was exposed to the current, wherein the self-assembled molecular structure is prepared from a compound comprising a methylene chain having between 10 and 25 carbon atoms.

2. The method of claim 1, wherein the self-assembled structure is prepared from a compound which includes at least one reactive functional group.

3. The method of claim 2, wherein the reactive functional group is selected from a group consisting of hydroxyl, carboxyl, sulfonyl, isocyanate, epoxy, amino, thiol, and acrylic.

4. The method of claim 1, wherein the self-assembled molecular structure is prepared from a compound selected from a group consisting of octadecyl isocyanate, dodecyl isocyanate, dodecanol, and 1-octadecanol.

5. The method of claim 1, wherein the polymer of the reservoir layer includes at least one reactive functional group.

6. The method of claim 5, wherein the reactive functional group is selected from a group consisting of hydroxyl, carboxyl, amino, and thiol.

7. The method of claim 1, wherein the polymer of the reservoir layer is selected from a group consisting of poly(ethylene-co-vinyl alcohol), poly(butyl methacrylate-co-2-hydroxyethyl methacrylate), poly(2-hydroxyethyl methacrylate), and poly(amino acid).

8. The method of claim 1, wherein the self-assembled structure comprises the following formula: $R-(CH_2)_n-R'$, wherein each of R and R' is independently a hydrogen, methyl, hydroxyl, carboxyl, sulfonyl, acetate, trifluoro acetate, benzoate, isocyanate, epoxy, amino, thiol, or acrylic group.

9. The method of claim 1, wherein the self-assembled structure comprises the following formula: $R-(CH_2)_n-R'$, wherein at least one of R or R' is a reactive group.

10. The method of claim 1, wherein the self-assembled structure comprises the following formula: $R-(CH_2)_n-R'$, wherein at least one of R or R' is an iscocyanate, epoxy or hydroxyl group.

11. The method of claim 1, wherein the self-assembled structure comprises a hydroxyl-terminated compound.

12. The method of claim 1, wherein the self-assembled structure comprises a isocyanate-terminated compound.

13. The method of claim 1, wherein the self-assembled structure comprises a carboxyl-terminated compound.

* * * * *